United States Patent [19]
Stone

[11] Patent Number: 4,964,404
[45] Date of Patent: Oct. 23, 1990

[54] BREATHING APPARATUS

[76] Inventor: William C. Stone, 7739 Laytonia Dr., Derwood, Md. 20855

[21] Appl. No.: 340,251

[22] Filed: Apr. 19, 1989

[51] Int. Cl.[5] .......... A61M 16/00; A62B 9/02

[52] U.S. Cl. .......... 128/204.22; 128/204.28; 128/204.29; 128/205.12; 128/205.13; 128/205.14; 128/205.17; 128/205.22; 128/205.24; 128/205.28; 128/206.15; 128/204.26; 2/2.5; 55/387

[58] Field of Search .......... 128/205.11, 205.12, 128/205.13, 205.14, 205.15, 205.17, 205.22, 205.24, 204.18, 204.22, 204.26, 204.28, 204.29, 201.25, 201.28, 206.15; 2/2.1 R, 2.1 A, 2.5; 55/387

[56] References Cited

U.S. PATENT DOCUMENTS

| | | | |
|---|---|---|---|
| 2,403,981 | 7/1946 | Jackson et al. . | |
| 2,710,003 | 6/1955 | Hamilton et al. . | |
| 3,111,946 | 11/1963 | Galeazzi . | |
| 3,129,707 | 4/1964 | Becker et al. | 128/205.22 |
| 3,351,089 | 11/1967 | Garrahan | 128/205.26 |
| 3,402,711 | 9/1968 | Emerson | 128/204.22 |
| 3,575,167 | 4/1971 | Michielsen . | |
| 3,656,196 | 4/1972 | O'Neill | 2/2.5 |
| 3,692,026 | 9/1972 | Tepper et al. | 128/204.28 |
| 3,710,553 | 1/1973 | Parker et al. . | |
| 3,837,337 | 9/1974 | Laviolette | 128/205.12 |
| 3,877,425 | 4/1975 | O'Neill | 128/204.22 |
| 3,891,996 | 7/1975 | Leach et al. | 2/2.5 |
| 3,929,127 | 12/1975 | Paul | 128/205.12 |
| 3,934,581 | 1/1976 | O'Neill | 128/205.22 |
| 4,056,098 | 11/1977 | Michel et al. | 128/204.28 |
| 4,068,657 | 1/1978 | Kobzan | 128/205.22 |
| 4,108,171 | 8/1978 | Wyman et al. | 128/204.26 |
| 4,163,448 | 8/1979 | Grouard . | |
| 4,181,126 | 1/1980 | Hendry | 128/201.21 |
| 4,266,539 | 5/1981 | Parker et al. . | |
| 4,273,120 | 6/1981 | Oswell . | |
| 4,299,216 | 11/1981 | Bernard | 128/205.12 |
| 4,304,229 | 12/1981 | Curtin . | |
| 4,409,978 | 10/1983 | Bartos | 128/205.12 |
| 4,423,723 | 1/1984 | Winkler et al. | 128/202.22 |
| 4,440,166 | 4/1984 | Winkler et al. | 128/204.22 |
| 4,454,878 | 6/1984 | Morrison | 128/204.22 |
| 4,567,889 | 2/1986 | Lehmann . | |
| 4,793,340 | 12/1988 | Ottestad | 128/200.24 |

FOREIGN PATENT DOCUMENTS

| | | | |
|---|---|---|---|
| 493840 | 9/1977 | Australia | 128/204.22 |
| 0079709 | 5/1983 | European Pat. Off. | 128/204.22 |
| 2491428 | 4/1982 | France | 128/204.22 |
| 2200288 | 8/1988 | United Kingdom | 128/204.28 |

OTHER PUBLICATIONS

"Design of Fully Redundant Autonomous Life Support Systems", article by William C. Sonte, Diving for Science, 1986, pp. 195–213.

*Primary Examiner*—Eugene H. Eickholt
*Attorney, Agent, or Firm*—Marks Murase & White

[57] ABSTRACT

A mixed gas breathing apparatus reversibly switchable between open circuit and closed circuit systems. Three embodiments show three different levels of redundancy: nonredundant, bi-linear redundant and fully redundant. The counterlung minimizes the static lung loading and thus decreases breathing resistance. Manual control system is readily accessible and allows control of addition of the breathing gases.

42 Claims, 11 Drawing Sheets

BREATHING APPARATUS

CROSS-REFERENCE TO RELATED APPLICATIONS

Reference is made to applicant's co-pending applications Ser. No. 07/340,250 entitled "BREATHING APPARATUS MOUTHPIECE" filed Apr. 19, 1989 and application Ser. No. 07/340,260 entitled "BREATHING APPARATUS GAS-ROUTING MANIFOLD" filed Apr. 19, 1989.

FIELD OF THE INVENTION

The present invention relates to portable life support systems used to sustain human respiration in locations where exposure to the environment would be fatal and in particular where there is a lack of immediate recourse to a safe-haven. These portable life support systems are free of safety umbilicals and larger environmentally controlled structures.

BACKGROUND OF THE INVENTION

Portable life support systems are used in a variety of situations in which the ambient environment around the user cannot be breathed either because of the lack of oxygen in usable form or because of the presence of substances which would have toxic effects if inhaled. These uses include extravehicular activity in space, scuba diving, deep off-shore diving work, use in contaminated atmospheres, use at high altitudes and the like.

The two fundamental architectures in the design of portable life support apparatus are open circuit and closed circuit systems. Open circuit systems, typified by the underwater diving system popularized by Jacques Cousteau, are the simplest, consisting of a compressed gas supply and a demand regulator from which the user breathes. The exhaust gas is ported overboard with each breath, hence the name "open" circuit. These systems are bulky and inefficient in that the oxygen not absorbed during each breath is expelled and wasted. Additionally failure of any component results in failure of the system.

Closed circuit systems, also known as rebreathers, make nearly total use of the oxygen content of the supply gas by removing the carbon dioxide generated by the user, and adding makeup oxygen or oxygen containing gas to the system when the internal volume drops below a set minimum level, or when the oxygen partial pressure drops below some pre-established setpoint.

These closed circuit breathing systems generally consist of a mouthpiece from which the user breathes and which is connected by means of two flexible impermeable hoses, one to remove the exhaled gas and the other to return the processed gas to a means for removing the carbon dioxide from the breathing gas, replenishing metabolized oxygen, and providing for makeup gas volume with a breathable gas to maintain system volume during descent as the gases within the breathing circuit are compressed. Such devices are usually provided with a series of checkvalves located near the mouthpiece such that gas flow within the breathing circuit is always maintained in a single direction. Oxygen addition to the system may be made by several means, most commonly by oxygen generators, such as the type disclosed in U.S. Pat. No. 2,710,003, to Hamilton et al., or the addition of oxygen or an oxygen containing gas, either through a constant mass flow orifice or by means of a manually operated or a sensor-controlled electronic valve.

Gas addition closed circuit systems may be one of two types, a pure oxygen version, which is limited to operating environments where the partial pressure of oxygen is less than two atmospheres, and a mixed gas version, normally used for underwater work at great depths. From a control standpoint, oxygen rebreathers are quite simple and require no active control. Mixed gas rebreathers, on the other hand, are considerably more complex. These were first pioneered in the late 1960's in an effort to solve the problems of narcosis at depths and to eliminate the oxygen toxicity problems which limit the safe diving depth of pure oxygen rebreathers.

The major deficiencies and problems existing with these known systems include a lack of redundancy or safety, limited duration or range, excess weight, high breathing resistance , and difficult manual operation.

A major leak anywhere in the breathing circuit of existing rebreathers leads to a subsequent flooding of the carbon dioxide removal system and therefore failure of the breathing apparatus. For operations conducted in locations where an immediate abort to a safe environment is impossible, such a failure could result in the death of the user.

When breathing in a closed circuit system, the exhaled breathing gas is held in a closed container, such as a breathing bag or a counterlung. Work is done when the gas is exhaled into, or inhaled from, the counterlung since surrounding environment is displaced as the counterlung is expanded. It has now been discovered that the work of breathing is dependent upon the user orientation angle and is directly related to static lung loading, which is the vertical distance, in centimeters of water, from the diver's or "user's" suprasternal notch, and the center of gravity of the inflated counterlung. Further, lung physiology prefers a slight positive pressure during inhalation, such as a static lung loading of between 0 to +10 centimeters of water. The present invention is the first to appreciate that known rebreathers with back-mounted counterlungs have negative static lung loadings and thus difficult inhalation characteristics while those that are chest-mounted have positive static lung loadings well in excess of +10 centimeters of water, and thus have hard exhalation characteristics. Furthermore, it has also been discovered that these known counterlungs are very sensitive to the user orientation angle due to the location of the center of gravity of these counterlungs.

In the prior art manual bypass valves, which permit the user to manually add either oxygen or an oxygen containing gas to the breathing circuit in the event of failure of the automatic valves, if present, have been placed on the body of the rebreather. For the case of a back-mounted rebreather, such as that shown in U.S. Pat. No. 3,710,553, these valves require an awkward reverse reach in order to operate them.

It is a primary object of the present invention to provide a mixed gas breathing apparatus switchably operable between open circuit and closed circuit modes and with different levels of redundancy for this apparatus; non-redundant, bi-linear redundant, and fully redundant.

It is a further object of the present invention to provide a counterlung for the breathing apparatus that minimizes the work of breathing wherein the static lung loading is between 0 to +10 centimeters of water.

A still further object of the present invention is to provide a manual control system which is compact and easy to reach. Such ease of use and ready accessibility is essential in an emergency where the user is apt to panic when faced with the possibility of death.

SUMMARY OF THE INVENTION

The present invention provides an integrated, improved mixed gas breathing apparatus which solves the specific problems described above. This mixed gas breathing apparatus is reversibly switchable between an open circuit and a closed circuit system. In three different embodiments of this invention, the breathing apparatus has different levels of redundancy. The first embodiment, as depicted in FIG. 1, is a non-redundant breathing apparatus. The second embodiment, depicted in FIG. 12, is a redundant bi-linear breathing apparatus. While, the third embodiment, depicted in FIG. 14, is a fully redundant breathing apparatus.

The breathing apparatus of the present invention is preferably equipped with twin, split counterlungs comprising the frontal portion of a vest worn by the user. An integral buoyancy compensator comprises the back side of the vest. The counterlungs are independently attached by means of flexible waterproof hoses to independent carbon dioxide removal systems in gas sensor banks for automated control of the oxygen concentration in each half of the system.

The breathing apparatus is equipped with two mouthpieces, for the bi-linear redundant and fully redundant systems, or one mouthpiece for the non-redundant system, connected by means of flexible waterproof hose to the independent split counterlungs, from which the user breathes and which can be made to function in either the open circuit or closed circuit mode. Each mouthpiece is equipped with directional check valves which control the direction of gas flow through the closed circuit system.

When used for diving, or under other pressure conditions, upon decent to greater depth or increased pressure, and in subsequent collapse of the counterlungs, inhalation demanded is satisfied through the mouthpiece, which contains an internal second stage open circuit diaphragm and gas addition valve which together comprise the automatic diluent system. The second stage diluent gas addition valve is equipped with an adjustable in-line flow restricter which permits the user to adjust the pressure drop required to trigger an opening of the valve and, should the need arise, completely close off the flow, thus providing diluent shut-off capability within easy, quick reach of the user.

Auxiliary manual control systems are provided for each closed circuit breathing circuit in compact cases which are affixed to the front of the vest. Each manual control system permits the user to manually add both oxygen and a diluent gas, as well as to shut-off the flow of oxygen to the breathing circuit from the automatic oxygen control system in the event of a malfunction in the automatic control system. Each manual control system output is connected by means of a single flexible low pressure line to the downstream side of the exhalation hose from each respective mouthpiece at its junction with the exhalation counterlung.

Two manifold blocks, mounted at the shoulder line of the vest, permit inhalation and exhalation lines from each mouthpiece, and automatic and manual gas addition lines, to be cross routed to the opposite system's carbon dioxide removing and gas control systems in the event of a malfunction.

BRIEF DESCRIPTION OF THE DRAWINGS

The invention is further described by way of the illustrative examples with reference to the drawings, in which.

DETAILED DESCRIPTION OF THE INVENTION

Figure 1:
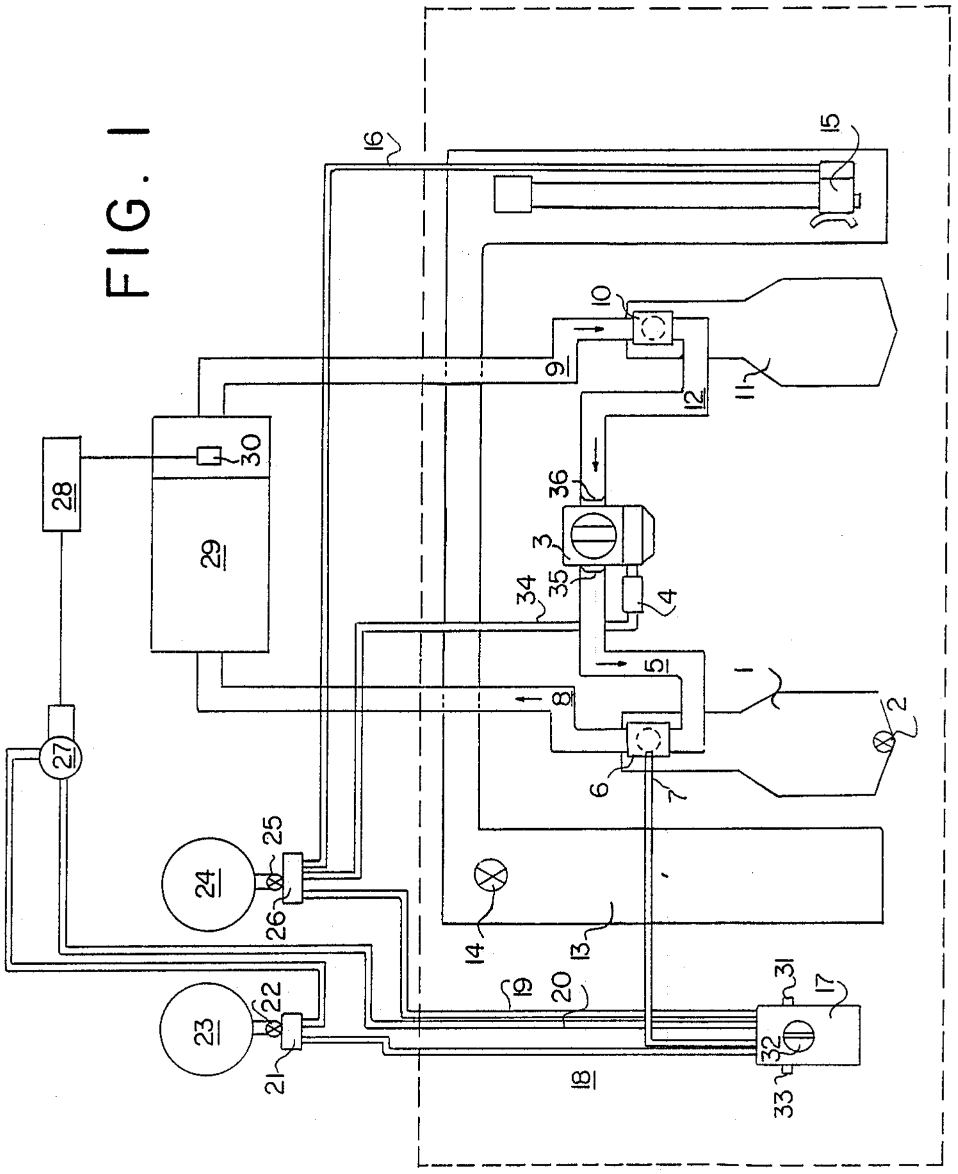
FIG. 1 is a schematic representation of a nonredundant sensor-controlled closed circuit mixed gas breathing apparatus of the present invention.

The non-redundant sensor-controlled closed-circuit mixed-gas breathing apparatus of the present invention is schematically shown in FIG. 1. In accordance with the invention, there is provided a mouthpiece 3 into which the user breathes. An example of such a mouthpiece which may be used is the subject of my co-pending application Ser. No. 07/340,250 entitled "BREATHING APPARATUS MOUTHPIECE" filed on Apr. 19, 1989 and which is incorporated herein by reference. The flow of the breathing gas is constrained in the direction of the arrow by checkvalves 35 and 36 on the exhale and inhale sides of mouthpiece 3 respectively. Upon exhalation, the flow is preferably directed through hose 5 and into manifold 6 where it is routed by means of an internal "T" joint into the user's right hand counterlung. The counterlung may have any desired configuration or shape. Preferably the counterlung is split into counterlungs 1 and 11, each having a capacity of about one-half the volume of the user's lung capacity. The exhaled gas in excess of that held by counterlung 1 flows through hose 8 and into a chamber 29 which contains a carbon dioxide removal system. The cleansed gas, from which the carbon dioxide has been removed, then continues through hose 9, into manifold 10, and consequently into counterlung 11, which comprises the second half of the counterlung volume. This completes the exhalation cycle.

Upon inhalation, the gas in the left hand counterlung 11 is breathed through hose 12, then checkvalve 36, into mouthpiece 3 until counterlung 11 collapses. At this point, the volume of counterlung 1 is drawn through the carbon dioxide removal system 29, through hose 9, and directly through manifold 10 to hose 12 to mouthpiece 3.

During normal operation of the apparatus oxygen is metabolized by the user and converted to carbon dioxide which is subsequently removed from the system. Provided depth is not increasing during this time, the partial pressure of oxygen will begin to decrease. An increase in depth results in an increase in the pressure, which includes an increase in the partial pressure of oxygen. The partial pressure of oxygen should be maintained between 0.14 and 1.4 atmospheres. A partial pressure of oxygen below 0.14 atmospheres will result in hypoxia while a partial pressure of oxygen above 1.4 atmospheres leads to central nervous system oxygen toxicity. Advantageously, an electrochemical sensor 30, or series of said sensors, may be provided to detect the partial pressure of oxygen and to provide information to an electronic decision making module 28, which may be either analog or digital. The sensor 30 is set at a pre-established setpoint, commonly 0.7 atmospheres, at which oxygen addition is triggered. When the partial pressure of oxygen indicated by sensor(s) 30 falls below this pre-established setpoint the electronic control system 28 opens an electronic valve 27, which subsequently permits a quantity of pressurized oxygen to be sent through a small diameter low pressure supply line 20 to the manual override control panel 17.

The pressurized oxygen supply which feeds electronic valve 27 preferably consists of a high pressure vessel 23, a shut-off valve 22, and a first regulator 21 which reduces the pressure sufficiently so that electronic valve 27 is operable. The pressure is typically reduced to about 10 bars. The flow of oxygen from electronic valve 27 to the breathing circuit may be stopped by the user at any time by closing manual valve 32 advantageously located in the center of the manual override panel 17, irrespective of whether valve 27 is open. This feature permits the user to take direct intervention and stop the flow of oxygen to the breathing circuit in the event of a failure of electronic valve 27 in the open position. Such failures in prior art devices can lead to the death of the user. A second low pressure oxygen line 18 carries oxygen directly from regulator 21 to the manual override control panel 17. There, lever 33, when depressed, actuates a manually operated valve which manually adds gas to the system and thus permits the user to continue operation in closed-circuit mode, even following failure of electronic valve 27. In a similar manner, diluent gas is provided for the system by means of a high pressure vessel 24, a shut-off valve 25, and a regulator 26 which reduces the pressure to a value typically supplied to second stage open-circuit regulators. This is typically about 10 bars. The diluent gas consists of oxygen and an inert, nontoxic gas or mixture thereof. Thus, the diluent gas may be air, a helium-oxygen mixture, nitrox, which is a combination of oxygen and nitrogen in proportions other than that of air, trimix, which is a combination of oxygen, nitrogen and helium, and the like.

Two low pressure, small diameter lines carry gas to the breathing circuit from the diluent supply. Line 34 connects the low pressure diluent output from regulator 26 with an adjustable, in-line control valve 4 which permits the user to adjust the pressure drop required to open a second stage open-circuit valve, which is integrated into mouthpiece 3. Adjustable valve 4 permits complete shut-off of the flow through feed line 34 thus allowing the user to stop a free flowing second stage valve in mouthpiece 3 without having to close the high pressure shut-off valve 25. Furthermore, an additional low pressure line 19 connects diluent regulator 26 to the manual override control panel 17. By depressing lever 31 the user can manually add diluent to the system irrespective of whether or not adjustable valve 4 is closed.

The output from the manual override control, (which includes oxygen delivered from electronic valve 27), is sent via a single low pressure line 7 to manifold 6 where it is injected into the closed-circuit process loop. Entry of the oxygen and diluent supply gases at this location ensures complete mixing prior to inhalation by the diver. Incomplete mixing can result in pockets of gas where there is too much or too little oxygen, thus possibly leading to hypoxia or oxygen toxicity.

From the above discussion, it is shown that there are two completely independent paths for both diluent and oxygen addition to the system, any of which can be shutdown or opened by means of manually controllable valves which are mounted on the user's chest, within easy reach and readily accessible.

A key safety feature of the present invention is that, in the event of total flooding of the closed-circuit process circuit described above, the user converts mouthpiece 3 to function as an open-circuit second stage regulator with no connection to the closed-circuit process loop. Use of a relatively large capacity diluent bottle 24, or an external diluent supply, can provide a significant amount of time for use of this integral open circuit bailout system, thus enabling the user to effect a recovery from the closed-circuit malfunction. This feature makes possible the safe use of the breathing apparatus of the present invention for general sport diving, where significant decompression is generally not a factor and where the open-circuit bailout system would permit a direct, safe ascent to the surface in the event of a failure of the closed-circuit portion of the apparatus.

The counterlungs consist of a closed volume which receives the exhalation gases and from which the inhalation gases are drawn. Advantageously, counterlungs 1 and 11 can be designed to form the front panels of a vest.

For diving use, the back panel of the same vest may advantageously be comprised of a buoyancy compensator 13 which is fabricated in a horseshoe shape not unlike that of a common back mounted buoyancy compensator used for open-circuit diving, except that it forms an integral portion of a hybrid vest. The buoyancy compensator portion of the vest is equipped with an oral/automatic inflator hose 15 for which low pressure diluent gas is supplied by low pressure line 16. Feed line 16 may either be connected to diluent regulator 26, or to an auxiliary external inflator bottle and regulator, not shown. Since both counterlungs 1 and 11, as well as buoyancy compensator 13 could burst due to expansion of gases during ascent, pressure relief valves 2 and 14 are provided for venting of the counterlungs and buoyancy compensator portions of the vest, respectively.

Figure 2:
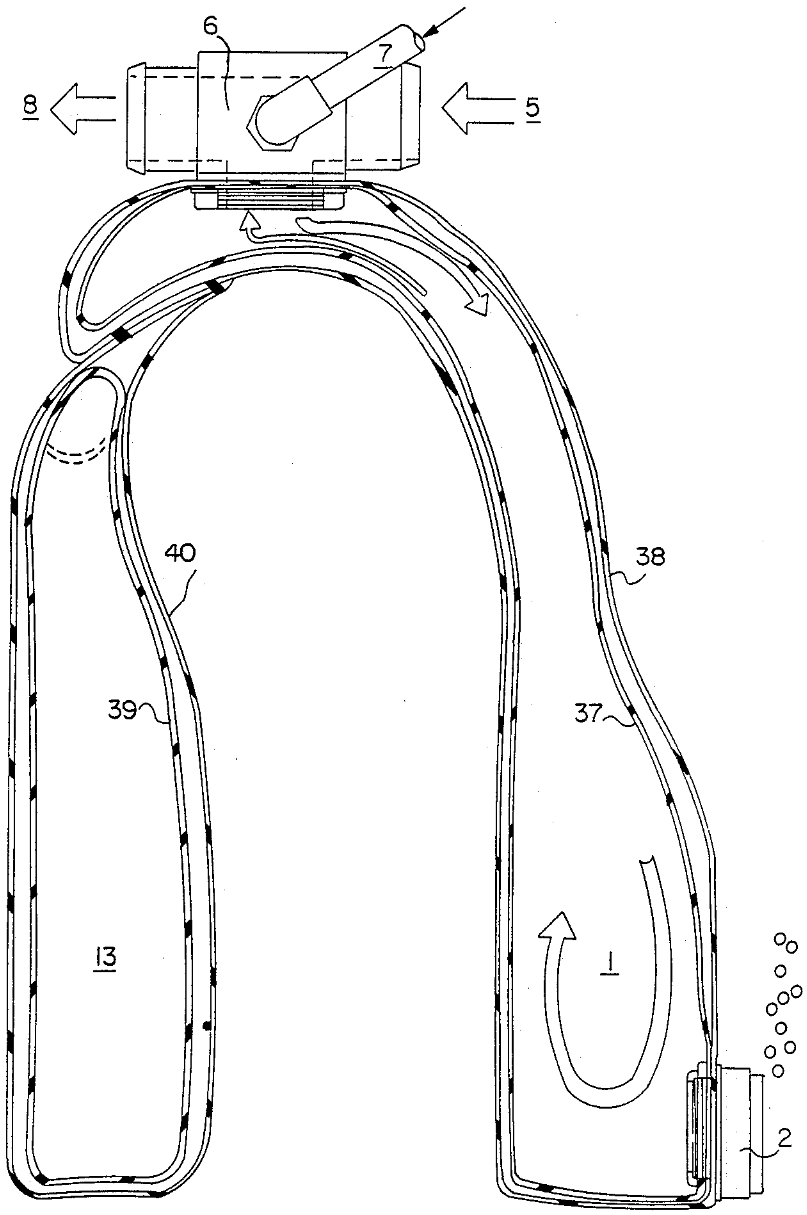
FIG. 2 is a lateral right hand sectional view of the integral buoyancy compensator/counterlung vest of the present invention with a unitary gas and liquid removal means.

FIG. 2 illustrates a lateral right hand view of such an integral buoyancy compensator/counterlung vest. The counterlung 1 is comprised of a flexible impermeable gas bag 37, which may be fabricated from any known material exhibiting the properties of flexibility and impermeability, such as latex rubber, neoprene rubber, urethane, or the like. Advantageously, gas bag 37 is protected by shell 38 which can be constructed from either a rigid material, such as injection molded plastic, or from a rugged flexible cloth, such as cordura nylon. The purpose of outer shell 38 is to protect gas bag 37 from puncture which would lead to subsequent flooding of the closed-circuit process system. In the event that protective shell 38 is constructed in a rigid form, vent holes are provided such that, when diving, the surrounding water may easily enter and leave the protective shell as the gas bag expands and contracts during breathing.

As shown in FIG. 2, counterlung 1 preferably forms the right hand front side of a vest to be worn by the diver. At the top of the diver's shoulder manifold 6 penetrates, and is sealingly connected to the internal gas bag 37, such that exhaled gas delivered through hose 5 may enter the gas bag. Manifold 6 contains an internal "T" joint configuration such that exhaled gas in excess of that required to fill gas bag 37 may pass directly through said manifold and into hose 8 which carries exhaled gas to carbon dioxide scrubber 29, depicted in FIG. 1. Thus, only one penetration of the gas bag 37 is required to permit ingress and egress of the gases.

Because the gases contained in gas bag 37 will expand when the outside ambient pressure is reduced, such as when a diver returns to the surface from depth or the user ascends into a higher altitude, an overpressure checkvalve 2 is provided to prevent bursting of gas bag 37. It may be noted that checkvalve 2 is advantageously located at the base of counterlung 1.

During general operation of closed-circuit diving apparatus it is not unusual for small amounts of water to seep into the mouthpiece, whereupon it is transported down the exhale hose 5 and into counterlung 1. The amount of water entering in this manner during a prolonged dive can be significant. Preferably checkvalve 2 is provided to automatically vent any water which has collected as the diver ascends and the gas in counterlung 1 expands to the point where checkvalve 2 is triggered to vent the overpressure. If checkvalve 2 is provided with an adjustable tension capability the diver may periodically lower the opening pressure for the checkvalve and manually compress counterlung 1 in order to expel the collected water.

Advantageously an integral buoyancy compensation unit 13 forms the back side of the vest when counterlung 1 forms the front portion of the vest with a slight overlap at the shoulder. Buoyancy compensator 13 may be fabricated in a manner analogous to that commonly used in the manufacture of back-mounted horseshoe shaped buoyancy compensators which include a flexible impermeable internal gas bag 39 and a flexible protective outer shell 40 both of which may be fabricated from the materials described above for counterlung 1. Buoyancy compensator 13 is attached to counterlung 1 as shown in FIG. 2 near the back of the diver's shoulder. The connection may be accomplished by any suitable means, such as by sewing the two outer shells 38 and 40 along the overlap area when flexible material is used for both protective shells, and by means of grommet holes and lacing where shell 38 is fabricated from a rigid material.

Figure 3:
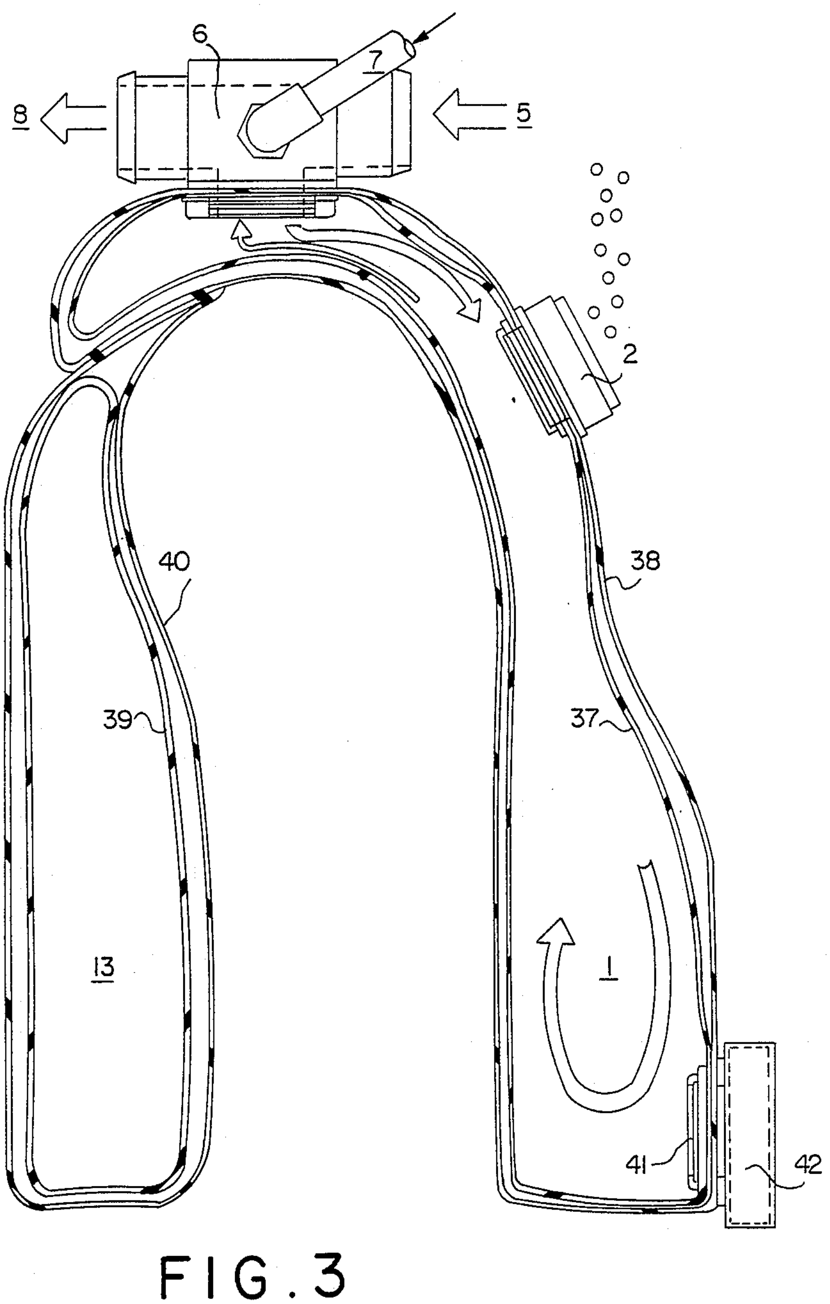
FIG. 3 is a lateral right hand sectional view of the integral buoyancy compensator/counterlung vest of the present invention with separate gas and liquid removal means.

A variation of the buoyancy compensator/counterlung vest of FIG. 2 is shown in FIG. 3 wherein checkvalve 2 is located near the diver's shoulder and a removable watertight canister 42 containing a moisture absorbing material is sealingly connected to penetration 41 which in itself penetrates and is sealingly connected to gas bag 37. This system, though less elegant than that shown in FIG. 2, since it involves three penetrations of gas bag 37 instead of two, allows for automatic removal of water from the counterlung without intervention from the diver. Absorbent cartridge 42 may be replaced between dives on the surface in a quick and easy manner. Checkvalve 2 must still be retained to prevent bursting of the counterlung 1 upon ascent from depth. Checkvalves for both counterlungs are not necessary as a single checkvalve 2 can control overpressure for both counterlung 1 as well as counterlung 11.

Figure 4:
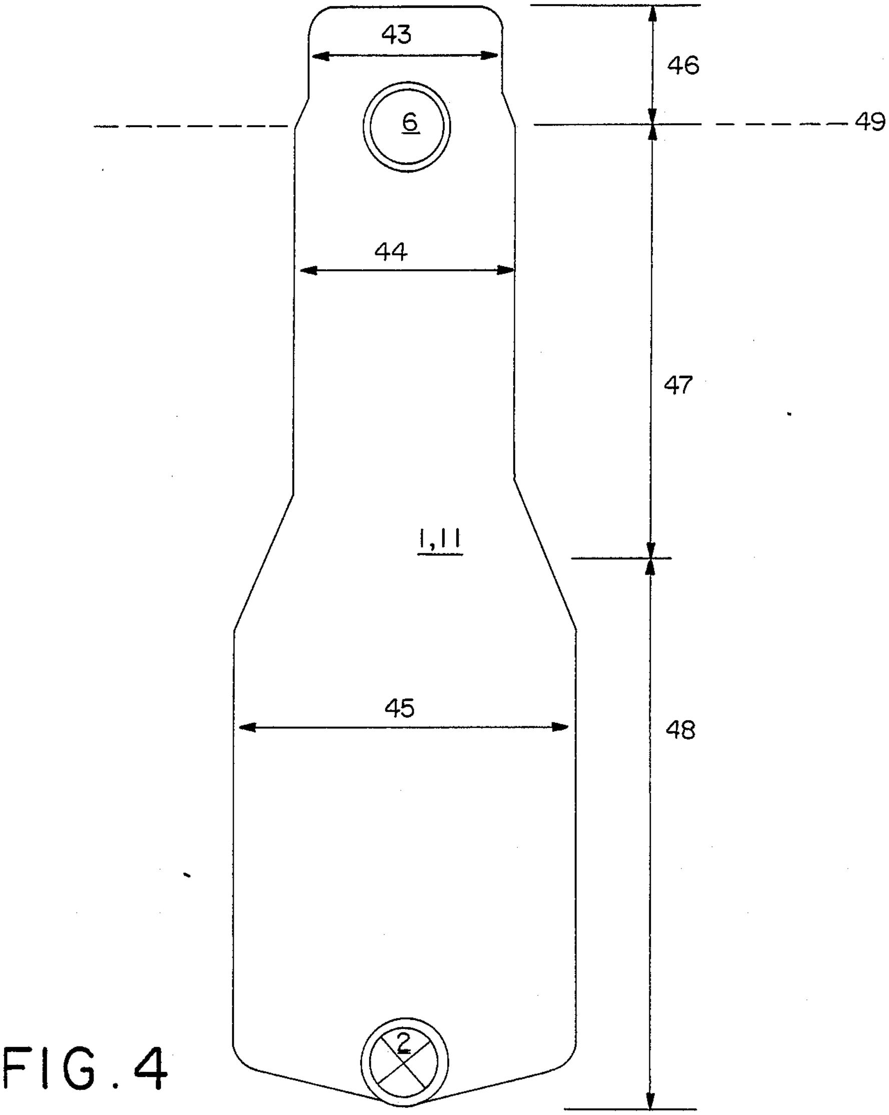
FIG. 4 is a top plan view of the counterlung of the present invention.

The counterlungs 1 and 11, as shown in FIG. 4, are preferably tapered in a specific manner. The segment of the counterlung of width 43 and length 46 extends behind diver's shoulder line 49. This is shown in FIGS. 2 and 3 as the short section of counterlung 1 which overlaps buoyancy compensator 13. A second segment extends from the diver's shoulder to a point partway down the diver's chest and contained within width 44 and length 47. A final, wider segment, bounded by width 45 and length 48 extends down the diver's chest below the second segment. Widths 43 through 45 are measured when gas bag 37 is laid flat. The circumference of the inflated gas bag in any given segment is thus 2 times the width value specified by widths 43, 44, or 45.

Figure 5:
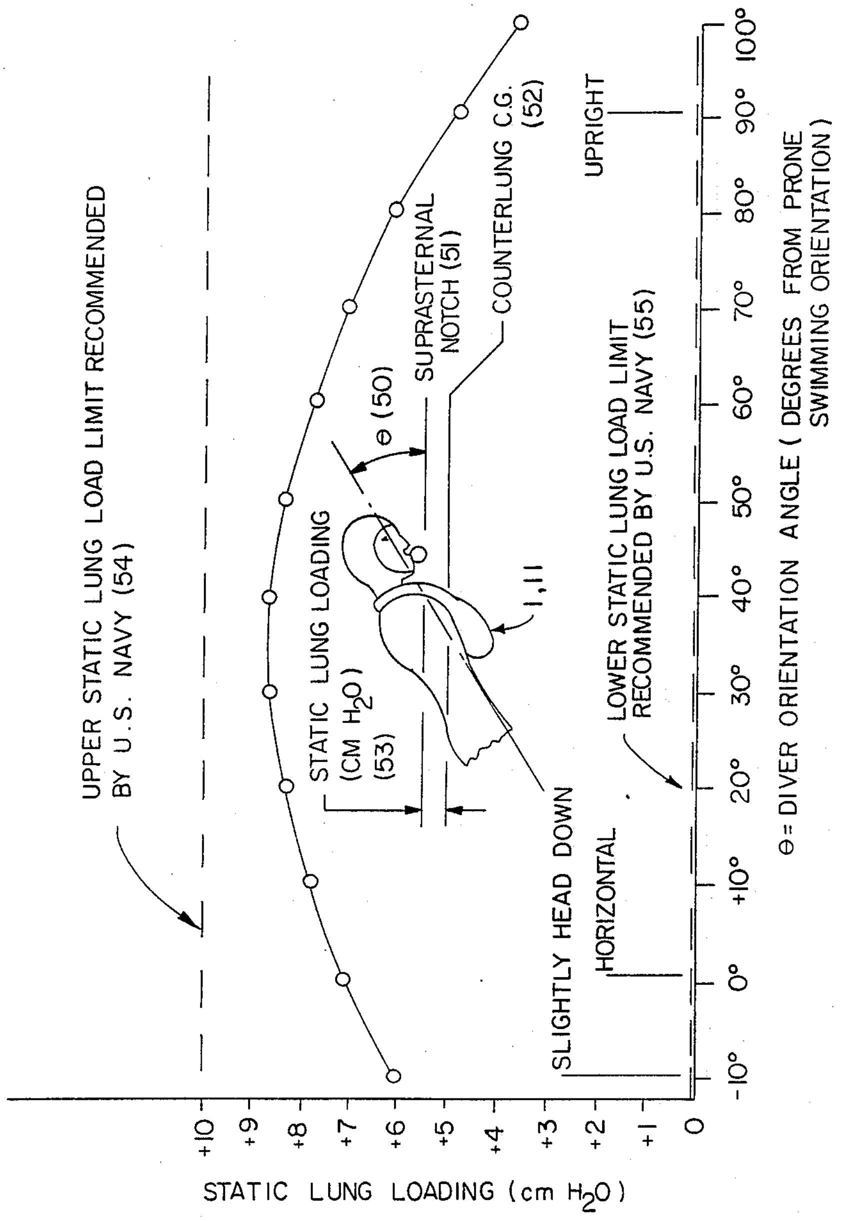
FIG. 5 is a graph illustrating the relationship between the user orientation angle and the static lung loading.

Referring to FIG. 5, for general diving operations a diver orientation angle 50 of between −30 degrees (head-down) to +120 degrees (leaning backward from vertical, looking upward) covers the entire range of normal and expected situations. Static lung loading 53 is equal to the difference in centimeters of water between the diver's suprasternal notch 51 and the center of gravity of the counterlung 52. As stated previously, it is highly desirable to have a slightly positive static lung loading, generally between 0 to +10 centimeters of water to reduce the breathing resistance and thus achieve easy work-of-breathing. An optimization computer program may be written which minimizes the static lung loading 53 throughout this regime of diver orientation angles by proper choice of counterlung dimensions 43 through 48.

For example, for a total counterlung capacity (both counterlungs 1 and 11) of 7 liters, an optimization to minimize static lung loading results in widths 43, 44, and 45, respectively, 10.2, 11.4, and 17.8 centimeters and lengths 46, 47, and 48, respectively, are 5.3, 22, and 24 centimeters. At the end of exhalation these dimensions will produce the curve plotted in FIG. 5 for static lung loading 53 versus diver orientation angle 50. From this it can be determined that the static lung loading is well within the desired upper 54 and lower 55 limits. It is desirable to design the counterlung such that static lung loading at the end of exhalation is shifted towards the upper limit 54, as shown by the curve plotted in FIG. 5 and as exemplified by the set of dimensions previously described, since the static lung loading will decrease slightly upon inspiration as the counterlung collapses. Significant extension of the counterlung segment bounded by width 43 and length 46 down the back side of the vest is non-productive, as this significantly decreases the positive static lung loading within the diver orientation angle regime desired by most divers.

It is to be noted that the counterlungs can be optimized for other diver orientation angles so that the static lung loading is at a minimum. Thus for example, where a diver is at an orientation angle of 180° degrees, such as would be used for work where a diver is underneath a ship doing repair work, counterlung dimension 46 may be extended in such a manner as to minimize the static lung loading.

For other uses the counterlung dimensions and placement may be adjusted. Thus, for example, for use in rescue work or in toxic environments at approximately atmospheric pressure, the location of the counterlung is not of the paramount importance that it is with diving work or other work under pressure. Thus, the counterlung may be located anywhere, although for convenience the vest form is best.

For deep space exploration work, the present invention may be used without separate independent counterlungs. Instead, the inside volume of the space suit serves as the counterlung.

For high altitude use, such as in mountain climbing, the counterlungs in a vest form, may be worn under the parka and other outer wear gear. This eliminates the internal frost buildup that has been a problem with known rebreathers for high altitude use.

Figure 6:
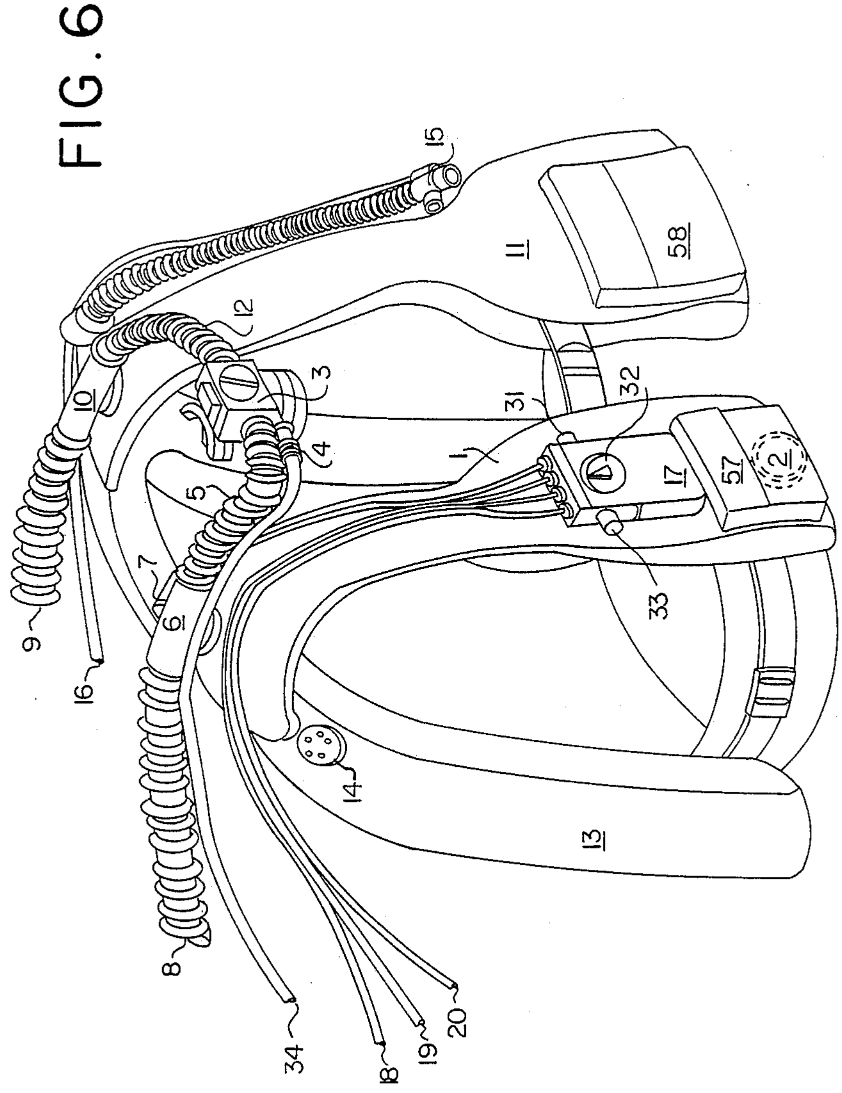
FIG. 6 is a perspective view of the breathing apparatus depicted in FIG. 1.

FIG. 6 is a perspective view of a physical rebreather incorporating the buoyancy compensator/counterlung vest thus far described as well as the special mouthpiece 3 and manual override control system 17 which will now be described in detail. As depicted in FIG. 6, there may be provided flexible utility pockets 57 and 58, which advantageously may be used to protect overpressure checkvalve 2 from abrasion.

Figure 7:
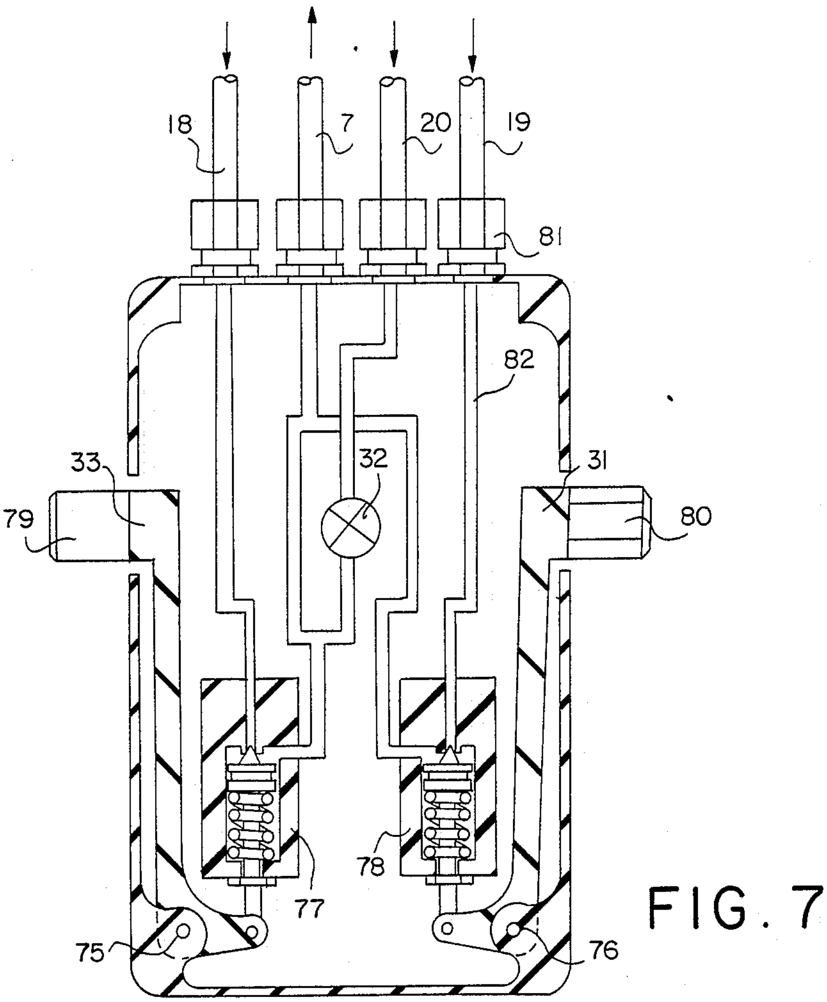
FIG. 7 is a front sectional view of the manual override control system of the present invention.

The manual override control system is illustrated in FIGS. 1 and 7. Preferably low pressure flexible hoses 18, 20 and 19 deliver direct oxygen from oxygen regulator 21, automatic control oxygen from electronic valve 27, and direct diluent from diluent regulator 26, respectively, to the bulkhead of case 17. Internal piping 82, which may be either flexible or rigid small diameter tubing, transfers gas from lines 18, 20, and 19 to control mechanisms. Line 18 carries oxygen to a normally closed, spring loaded valve 77 of a type that is commonly available. At the user's discretion, lever 33, which pivots on hinge 75, is depressed, thus opening valve 77 and permitting the passage of oxygen. In a similar manner, line 19 carries diluent to a normally closed, spring loaded valve 78. When lever 31, which pivots on hinge 76, is depressed, valve 78 is opened permitting the passage of diluent gas. Line 20 carries oxygen from the electronic oxygen addition valve 27 to a manually operable inline shut-off valve 32 which is left in the open position during normal conditions. It should be noted that valve 32, which is a one-quarter turn on-off valve commonly available, permits the user to rapidly stop the flow of oxygen from the electronic oxygen addition valve 27 in the event of a failure of valve 27 in the open position. The outputs of valves 32, 77 and 78 are piped such that only one common output 7 leaves the manual override control box 17. It should be also noted that levers 33 and 31 may be equipped with identification knobs 79 and 80, respectively, which permit the user to distinguish the oxygen and diluent addition levers by touch. For example, a knurled knob 79 may be used to indicate oxygen, while a hexagonal bar 80 may be used to indicate diluent. Other valves and means for regulating the gas flow may be used.

Figure 8:
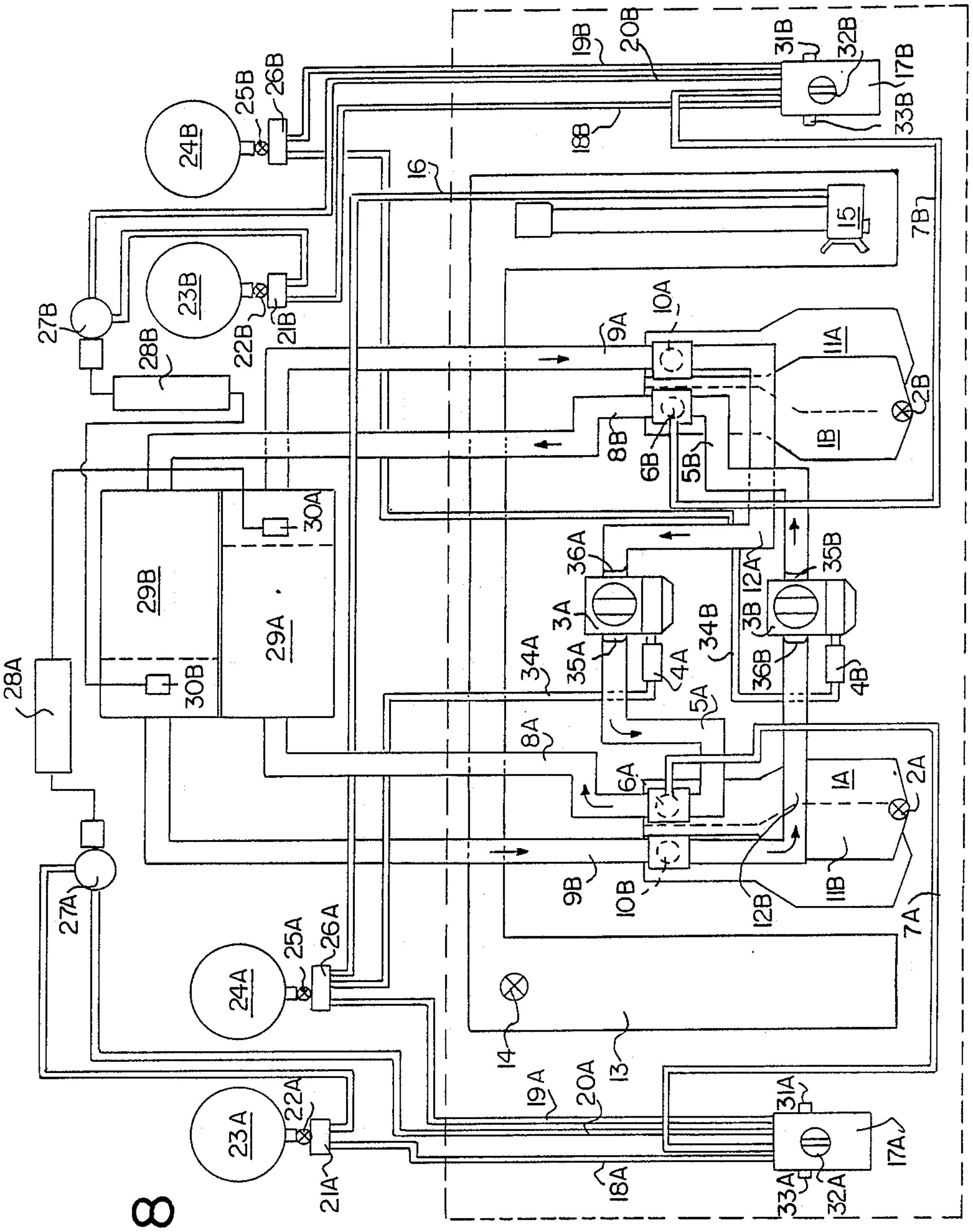
FIG. 8 is a schematic representation of a redundant bi-linear sensor-controlled closed circuit mixed gas breathing apparatus of the present invention.

The second embodiment of the invention, the bi-linear redundant mixed gas breathing apparatus, is schematically illustrated in FIG. 8.

The component numbers are the same for all figures. The addition of the letters A or B to a component number indicates which of the closed-circuit systems, either system A or system B, is referred to.

This closed-circuit system has several key characteristics which distinguish this system from the nonredundant systems previously described. First, because of the compact shape of counterlungs 1 and 11, and because they principally occupy space on the user's chest and are generally not used simultaneously, it is possible to construct a hybrid vest in which the counterlungs from the two separate systems may be almost totally overlapped with the exception of their respective manifold ports 6 and 10. This permits the construction of a dual-system of independent split counterlungs which, together with a single buoyancy compensator 13 as previously described, comprise a vest that occupies a volume only nominally larger than that for the non-redundant system, as depicted in FIGS. 1 and 6. Preferably the two counterlungs comprising each vest panel, for example, 1A and 11B in FIG. 8 are fabricated such that they act structurally as a single unit. This may be accomplished, in the case of a flexible protective counterlung shell 38 by sewing or otherwise fastening the outer protective shells 38 for counterlungs 1A and 11B along the dashed and solid lines depicting the inner edge of counterlung 11B and the left-most edge of counterlung 1A, respectively, in FIG. 8.

Figure 9:
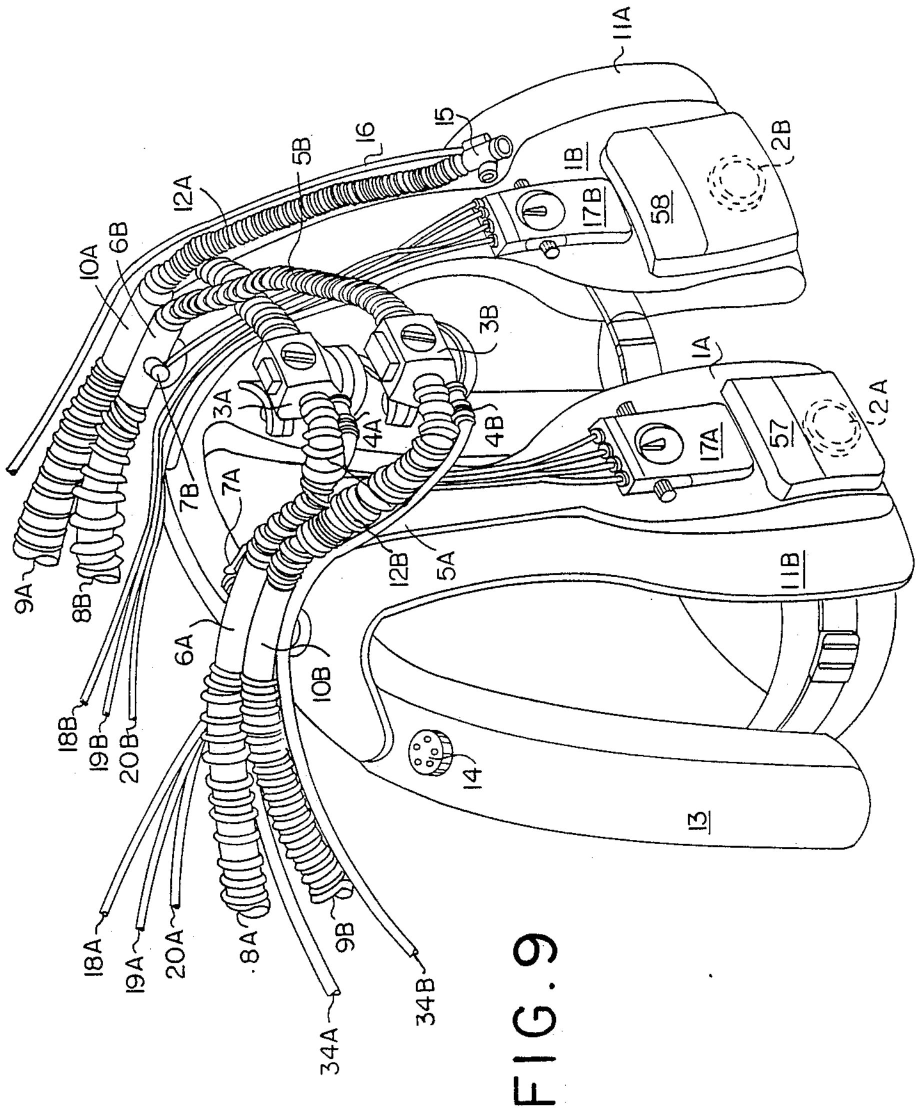
FIG. 9 is a perspective view of the breathing apparatus depicted in FIG. 8.

The two independent closed-circuit systems A and B may be constructed with either counter-rotational flow or corotational flow. Counter-rotational flow, as indicated by the arrows in FIG. 8, preserves external symmetry from the user's point of view, thus cleanly separating the functional operation of the two systems. This characteristic is further illustrated as follows. The exhalation counterlung 1A for system A is shown in FIG. 8 as the outer portion of the right hand vest panel. The inner portion of this same vest panel is comprised of the inhalation counterlung 11B for system B. In a similar manner, exhalation counterlung 1B for system B forms the outer portion of the left hand vest panel. The inhalation counterlung 11A forms the interior portion of the left hand vest panel. Because the exhalation counterlungs for both system A and system B comprise the outer elements of the vest panels, overpressure checkvalves 2A and 2B may be symmetrically placed as shown in FIG. 8. In addition, manual override panels 17A and 17B are preferably mounted on the exterior panels 1A and 1B, respectively. FIG. 9 shows a perspective view of the physical invention bounded by the dashed box in FIG. 8. In FIG. 9, it is evident in order to implement the architecture illustrated in FIG. 8, that inhalation hose 12A and exhalation hose 5B must cross.

From a system survival standpoint, the bi-linear redundant system illustrated in FIG. 9 provides a system survival probability in closed-circuit mode of approximately an order of magnitude greater than that for a non-redundant system, such as shown in FIG. 1. In the event of a failure of system A, for example due to flooding of system A, the user may simply switch from mouthpiece 3A to mouthpiece 3B and continue in a fully closed-circuit mode. Furthermore, in the event of failure of both closed-circuit systems, the user still has two independent diluent supplies which may be accessed in open circuit mode.

The second embodiment of the invention shown in FIG. 8, although substantially safer than any closed-circuit diving apparatus described in the prior art, may be further improved from a safety standpoint as described below.

Figure 10:
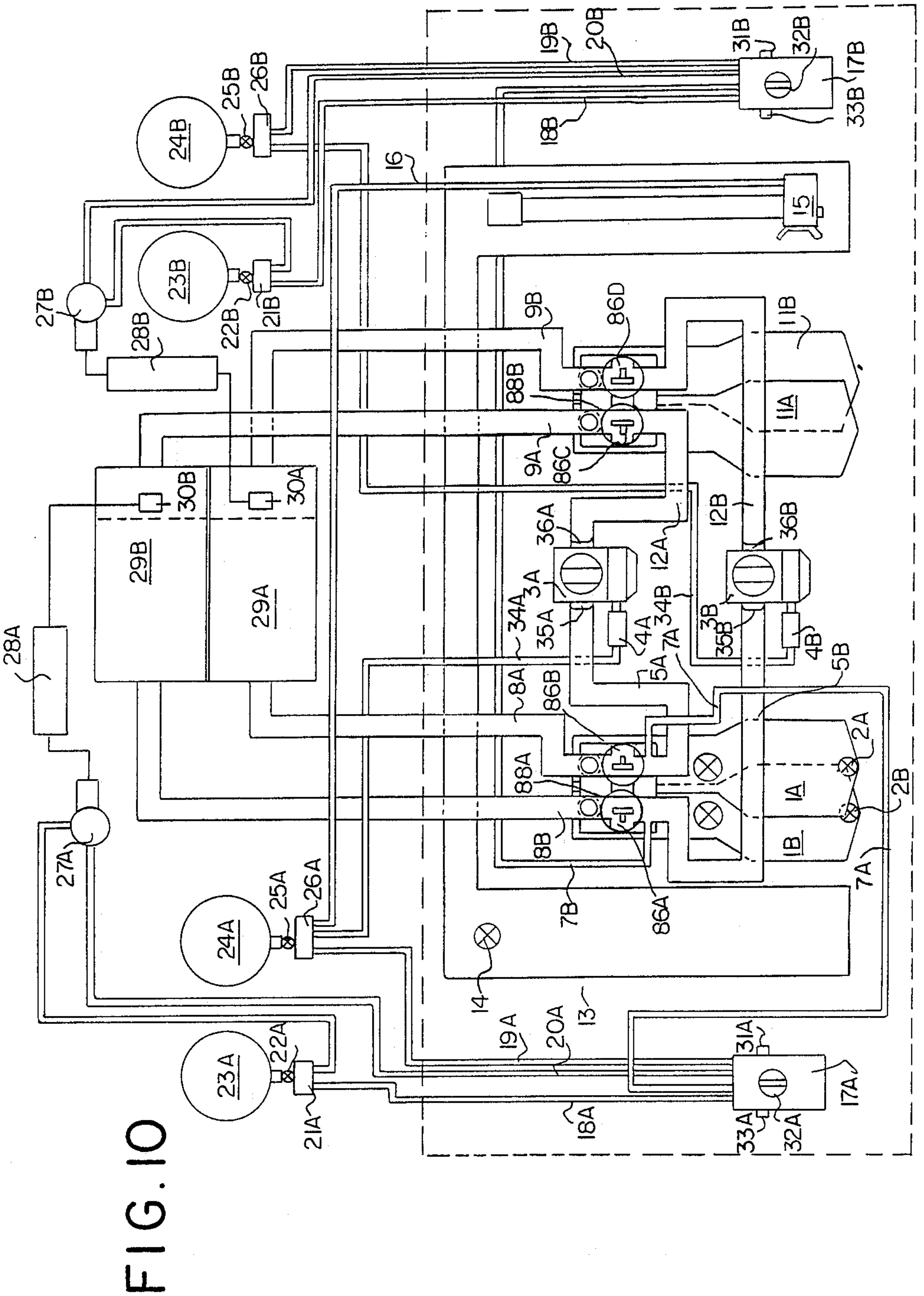
FIG. 10 is a schematic representation of a fully-redundant breathing apparatus of the present invention.

The third embodiment of the invention, a fully redundant closed-circuit diving apparatus, is depicted in FIG. 10. This differs from the second embodiment of the invention presented in FIG. 8 in several ways. First, the flow in the two independent closed-circuit systems A and B must be corotational, as indicated by the arrows in FIG. 10. The reason for this requirement is that the exhaled gases from both mouthpieces are now connected to an exhalation routing manifold 88A, mounted on the diver's right shoulder, which permits the diver to re-route the flow of the exhaled gas from either of mouthpiece 3A or mouthpiece 3B to its opposite system gas processing unit. A similar inhalation routing manifold 88B is provided on the diver's left shoulder such that the output from either gas processing system can be routed to any of mouthpieces 3A or 3B. For the sake of discussion, the terms "left shoulder" and "right shoulder" are used to describe the operation of the breathing apparatus of the present invention and can be interchanged, provided correct continuity is maintained with respect to gas flow direction.

These manifolds are further described in detail in my co-pending application Ser. No. 07/340,260 filed on Apr. 19, 1989 and incorporated herein by reference.

These routing manifolds allow the user to gain significant extra time by cross routing of the gases. For example, if all supply gases in system A have been exhausted, yet the carbon dioxide scrubber 29A still has useful life, the gases from mouthpiece 3B may be routed into carbon dioxide scrubber 29A, provided supply gas still exists in system B. The inhalation routing manifold 88B is identical to exhalation routing manifold with the exception that the gas addition bulkhead penetrations are not required. Also, both mouthpieces 3A and 3B may be routed to access carbon dioxide removal and oxygen control system B simultaneously. The exhalation flow from either mouthpiece may be completely blocked off. This may be desirable if a leak has occurred in one mouthpiece but the user needs the extra breathing time afforded by making use of the corresponding carbon dioxide removal system by means of the other mouthpiece. Alternate routing may include from one mouthpiece to the other carbon dioxide processing system. Valve positions for the inhalation manifold 88B are identical to those for manifold 88A. These valves are identified as 86C and 86D in FIG. 11, a perspective view of the fully redundant embodiment of the invention.

Figure 11:
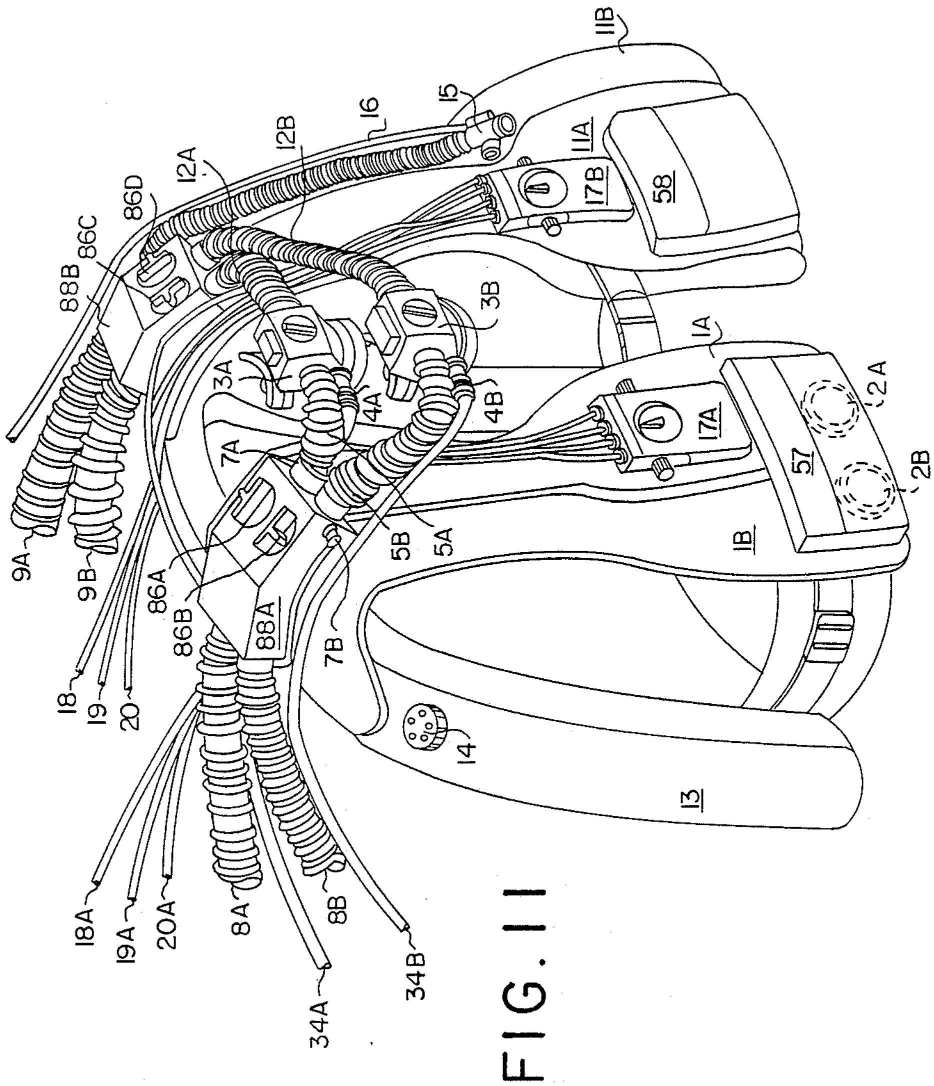
FIG. 11 is a perspective view of the fully-redundant breathing apparatus depicted in FIG. 10.

In FIG. 11 it should be noted that although overpressure checkvalve 2B is located at the bottom of counterlung 1B, it could equally well be located on counterlung 11B. In FIG. 11 both overpressure checkvalves 2A and 2B may be protected from abrasion by being placed underneath flexible utility pocket 57. An additional flexible utility pocket 58 may be provided at the bottom of counterlung 11A.

It should be understood that the foregoing disclosure relates only to preferred embodiments of the invention and that numerous modifications or alterations may be made therein without departing from the spirit and scope of the invention as set forth in the appended claims.

I claim:

1. A breathing apparatus comprising:

a first circuit comprising:
  a mouthpiece;
  a counterlung;
  a carbon dioxide removal device;

said first circuit being operatively connected to enable gas to flow from said mouthpiece to said counterlung and said carbon dioxide removal device and back to said mouthpiece; and further comprising:

a second circuit comprising:
  a supply of breathable gas normally automatically supplied to said first circuit over a first path;
  a manual override system for manually interrupting said automatically supplied breathing gas; and
  a second path for selectively manually connecting said supply of breathable gas to said first circuit through said manual override system for selectively manually admitting breathable gas into said first circuit.

2. The breathing apparatus of claim 1 further comprising a second closed circuit breathing apparatus, essentially identical to the first mentioned closed circuit breathing apparatus and connected in parallel with said first mentioned closed circuit breathing apparatus and wherein the counterlung members of said first and second closed circuit breathing apparatus comprise a unitary member.

3. A redundant closed circuit breathing apparatus having two independent closed circuit systems each of said systems comprising:

a first circuit comprising:
  a mouthpiece;
  a counterlung;
  a carbon dioxide removal device;
  a path for flowing gas from said mouthpiece to said counterlung and said carbon dioxide removal device and back to said mouthpiece; and a second circuit comprising:
  a supply of breathable gas;
  a manual override valve;
  a second path for selectively connecting said supply of breathable gas to said first circuit through said manual override valve for selectively admitting breathable gas into said closed circuit;
  an exhaust gas routing manifold for selectively routing exhaled gas from the mouthpiece of either one of said two independent closed circuit systems to the carbon dioxide removal device of either one of said two independent closed circuit systems; and
  an inhalation gas routing manifold for selectively connecting the carbon dioxide removal device of either one of said two independent closed circuit systems to the mouthpiece of either one of said two independent closed circuit systems.

4. The breathing apparatus of any of claims 1, 2, or 3 further comprising a vest, said vest including a front portion comprising said counterlung adapted to be worn on a front portion of a user's torso and a back portion comprising a buoyancy compensator adapted to be worn on a back portion of a user's torso.

5. The breathing apparatus of any of claims 2 or 3 wherein said mouthpiece further includes a check valve for controlling the direction of gas flow through said first circuit.

6. The breathing apparatus of any of claims 1, 2 or 3 further comprising means for selectively switching said mouthpiece into and out of said first circuit.

7. The breathing apparatus of any of claims 1, 2 or 3 further comprising an oxygen sensor for detecting the partial pressure of oxygen of the breathable gas in the first circuit and means responsive to said oxygen sensor for admitting breathable gas from said supply of breathable gas into said first circuit when said partial pressure falls below a pre-established set point.

8. The breathing apparatus of claim 4 further comprising a pressurized gas source and a valve for selectively connecting said pressurized gas source to said buoyancy compensator to admit gas into said buoyancy compensator.

9. The breathing apparatus of any of claims 1, 2, or 3 wherein said supply of breathable gas comprises a diluent gas source and an oxygen source.

10. The breathing apparatus of claim 4 wherein said supply of breathable gas comprises a diluent gas source and an oxygen source.

11. The breathing apparatus of claim 10 further comprising a valve for selectively connecting said diluent gas supply to said buoyancy compensator.

12. The breathing apparatus of claim 1 wherein said counterlung contains valve means mounted on said counterlung to automatically expel water contained in said counterlung and for preventing overpressurization.

13. The breathing apparatus of any of claims 2 or 3 wherein at least one of said counterlungs contains a relief valve for preventing overpressurization.

14. The breathing apparatus of any of claims 1, 2 or 3 further comprising venting means mounted on said counterlung for automatically removing water from said counterlung.

15. The counterlung of claim 14 wherein said counterlung is a split counterlung.

16. The counterlung of claim 15 wherein said split counterlung forms a vest adapted to be worn by the user.

17. The counterlung of claim 14 wherein said counterlung is formed from a flexible, gas impermeable material.

18. The counterlung of claim 17 wherein said flexible and impermeable material is selected from the group consisting of latex rubber, neoprene rubber, and polyurethane.

19. A counterlung for a closed circuit breathing apparatus, said counterlung having a first portion adapted to extend behind a user's shoulderline; a second portion contiguous with said first portion and adapted to extend from approximately the user's shoulder at least part way along the user's chest; and a third portion, contiguous with said second portion and adapted to extend along the user's chest below said second portion; said counterlung when inflated, having a center of gravity having a positive pressure from about 0 to 10 cm of $H_2O$, measured relative to the user's suprasternal notch.

20. A closed circuit breathing apparatus comprising:
a first circuit comprising:
a mouthpiece;
a counterlung;
a carbon dioxide removal device;
a path for flowing gas from said mouthpiece to said counterlung and said carbon dioxide removal device and back to said mouthpiece; and
a second circuit comprising:
a supply of breathable gas;
a manual override valve; and
a second path for selectively connecting said supply of breathable gas to said first circuit through said manual override valve for selectively admitting breathable gas into said closed circuit;
further comprising venting means for removing water from said counterlung;
wherein said counterlung is formed from a flexible, gas impermeable material;
further comprising a rigid injection molded plastic outer shell for protecting said flexible gas impermeable material.

21. A closed circuit breathing apparatus comprising:
a first circuit comprising:
a mouthpiece;
a counterlung;
a carbon dioxide removal device;
a path for flowing gas from said mouthpiece to said counterlung and said carbon dioxide removal device and back to said mouthpiece; and
a second circuit comprising:
a supply of breathable gas;
a manual override valve; and
a second path for selectively connecting said supply of breathable gas to said first circuit through said manual override valve for selectively admitting breathable gas into said closed circuit;
further comprising a venting means for removing water from said counterlung;
wherein said counterlung is formed from a flexible gas impermeable material;
further comprising a tear resistant, flexible cloth outer shell for protecting said flexible, gas impermeable material.

22. A manual override control system for a breathing apparatus having a breathable gas supply, and a closed circuit including a mouthpiece, counterlung, and carbon dioxide removal device, said manual override control system comprising:
a housing;
an input to said housing for admitting breathable gas from said breathable gas supply thereto;
an output from said housing for directing said breathable gas to said closed circuit;
a flow path connecting said input to said output; and
a manually operable valve disposed in said gas flow path for selectively opening and closing said flow path;
wherein said breathable gas supply comprises a diluent gas source and an oxygen source and said input comprises a first input from said diluent gas source and a second input from said oxygen source;
further wherein said manually operable valve comprises a first spring loaded spring valve for selectively opening said flow path for said oxygen source and a second spring loaded valve for selectively opening said flow path for said diluent gas source.

23. The manual override control system of claim 22 wherein said spring loaded valves are operable by means of a manually operated lever.

24. The manual override control system of claim 23 wherein said levers include means for distinguishing said oxygen and diluent addition levers by touch.

25. The manual override control system of claim 24 wherein said distinguishing means comprises a knurled knob to indicate said oxygen source and a hexagonal knob to indicate said diluent gas source.

26. The manual override control system of claim 22 wherein said housing is adapted to be disposed on the user's chest in a readily accessible location.

27. In a closed circuit breathing apparatus comprising a first source of gas, a second source of gas and a third source of gas, a mouthpiece having an inhalation side and exhalation side operatively connected to normally automatically receive gas from said third gas source, a first counterlung, a second counterlung, and a carbon dioxide removal device, a manual override control system for manually overriding said third source of gas, said system comprising:

first manually operable means for selectively manually allowing a flow of gas from said first gas source to said second counterlungs;

second manually operable means for selectively manually allowing a flow of gas from said second gas source to said second counterlung;

third manually operable means for selectively manually interrupting a flow of gas from said third gas source to said second counterlung;

housing means for housing said first, second and third manually operable means.

28. A control system for use with a breathing circuit comprising a mouthpiece having an inhalation side and an exhalation side, the inhalation side being connected to a first counterlung, the exhalation side being connected to a first valve having at least one input connected to said exhalation side and two outputs, one output being connected to a second counterlung and the other output being connected to an input of a carbon dioxide removal device, an output of said removal device being connected to said first counterlung, said control system comprising:

a first source of gas;

first shut-off valve means having an input connected to said first source, and an output, for manually permitting or preventing a flow of gas from said first source;

second valve means connected to said output of said first valve means;

sensor means associated with said removal device for sensing an amount of gas;

control means, responsive to said sensor means, for controlling said second valve means to permit or prevent a flow of gas from said first valve means; and manual interrupt means operatively positioned between said second valve means and said mouthpiece for selectively manually interrupting a flow of gas from second valve means to said mouthpiece.

29. The control system of claim 28 further comprising a first manually operable control means, operatively positioned between said first valve means and said mouthpiece, for selectively manually permitting a flow of gas from said first valve means to said mouthpiece.

30. The control system of claim 28 further comprising:

a second source of gas;

a second manually operable control means, operatively positioned between said second source of gas and said mouthpiece for selectively manually permitting a flow of gas from said second source to said mouthpiece.

31. The control system of claim 30 wherein said manual interrupt means, first manually operable control means and second mutually operable control means are operatively mounted on the same housing.

32. The control system of claim 28 wherein said second valve means comprises an electronically controlled valve, said sensor means comprises an electrochemical sensor and said control means is an electronic control means.

33. The control system of claim 30 wherein said first and second manually operable control means each comprise a lever which when actuated, opens a normally closed, spring biased valve; and said manual interrupt means comprises a one-quarter turn on-off valve.

34. An integral counterlung/buoyancy compensator vest for use in a breathing system, said vest comprising:

a front portion;

a back portion;

said front portion comprising counterlung means operatively connected to said breathing system; and said back portion comprising at least a portion of a buoyancy compensator device.

35. An integral buoyancy compensator/counterlung vest adapted to be worn by a user, said device comprising:

counterlung means comprising a flexible, gas impermeable bag, said counterlung means forming substantially a front portion of said vest; and buoyancy compensator means, attached to a portion of said counterlung means, comprising a flexible gas impermeable bag, said buoyancy compensator means comprising substantially a back portion of said vest.

36. The vest of any of claims 34 or 35 wherein said counterlung means comprises a split counterlung comprising a first counterlung and a second counterlung.

37. The vest of claim 36 wherein each of said first counterlung and second counterlung comprises:

a first segment having a first width and a first length, said first width and length being such that said first segment is adapted to extend from an area behind a user's shoulder line to an area of a user's shoulder and provide an area of overlap with said buoyancy compensator means;

a second segment having a second width and a second length, said second segment adapted to enable said second segment to extend from the area of a user's shoulder to an area partway down a user's chest; and a third segment having a third width and a third length, said third segment adapted to enable said third segment to extend from an area partway down a user's chest to an area near a user's waist.

38. The vest of claim 35 further comprising protection means for surrounding and protecting said counterlung means and buoyancy compensator means.

39. The vest of claim 37 wherein said buoyancy compensator means overlaps with a portion of said first segment and extends from said first segment to an area at the back of a user's waist.

40. The vest of claim 37 wherein said first, second and third widths, and said first, second and third lengths are selected such that for a diver orientation angle between −30 degrees and +120 degrees, the static lung loading of the counterlung means is in the range of 0 to +10 centimeter.

41. The vest of claim 37 wherein said counterlung means has a total capacity of approximately seven liters, said first, second and third widths are approximately 10.2, 11.4 and 17.8 centimeters, respectively; and said first, second and third lengths are approximately 5.3, 22.0 and 24.0 centimeters, respectively.

42. The counterlung of claim 21 wherein said tear resistant, flexible cloth is selected from the group consisting of cordura nylon or ballistics nylon.

* * * * *